(12) United States Patent
Smyth et al.

(10) Patent No.: US 7,747,068 B1
(45) Date of Patent: Jun. 29, 2010

(54) SYSTEMS AND METHODS FOR TRACKING THE EYE

(76) Inventors: Andrew Paul Smyth, 2712 Park Shire Rd., Fallston, MD (US) 21047;
Christopher Charles Smyth, 2712 Park Shire Rd., Fallston, MD (US) 21047

( * ) Notice: Subject to any disclaimer, the term of this patent is extended or adjusted under 35 U.S.C. 154(b) by 747 days.

(21) Appl. No.: 11/340,821

(22) Filed: Jan. 20, 2006

(51) Int. Cl.
G06K 9/00 (2006.01)
G03B 17/00 (2006.01)

(52) U.S. Cl. .......................... 382/154; 396/51
(58) Field of Classification Search ................ 382/154; 396/51; 351/209, 210; 600/558; 348/E13.041, 348/E13.047
See application file for complete search history.

(56) References Cited

U.S. PATENT DOCUMENTS

| | | | | |
|---|---|---|---|---|
| 4,973,149 A | | 11/1990 | Hutchinson | 351/210 |
| 5,583,795 A | * | 12/1996 | Smyth | 702/150 |
| 5,719,954 A | * | 2/1998 | Onda | 382/154 |
| 5,984,475 A | | 11/1999 | Galiana et al. | 351/209 |
| 6,120,461 A | | 9/2000 | Smyth | 600/558 |
| 6,198,484 B1 | | 3/2001 | Kameyama | 345/419 |
| 6,568,809 B2 | | 5/2003 | Trajkovic et al. | 351/209 |
| 6,603,491 B2 | * | 8/2003 | Lemelson et al. | 715/784 |
| 7,237,898 B1 | * | 7/2007 | Hohla et al. | 351/246 |
| 2002/0154269 A1 | * | 10/2002 | Liu et al. | 351/206 |
| 2005/0175218 A1 | * | 8/2005 | Vertegaal et al. | 382/103 |

OTHER PUBLICATIONS

A. C. Cook, T. Day, and J-P. Muller. The UCL IUS-Tithonium Chasma Digital Elevation Model.Jul. 18-23, 1999. Fifth International Conference on Mars. Center for Earth and Planetary Studies, National Air and Space Museum, Washington DC 20560, USA.*
L. P. Adams, "X-ray stereo photogrammetry locating the precise, three dimensional position of image points," Med. Biol. Eng. Comput., vol. 19, pp. 569-578, 1981.*

* cited by examiner

Primary Examiner—Charles Kim
Assistant Examiner—Nirav G Patel (57) ABSTRACT

Disclosed are systems and methods for tracking the eye. In one embodiment, a method for tracking the eye includes acquiring stereo images of the eye using multiple sensors, isolating internal features of the eye in the stereo images acquired from the multiple sensors, and determining an eye gaze direction relative to the isolated internal features.

19 Claims, 6 Drawing Sheets

SYSTEMS AND METHODS FOR TRACKING THE EYE

GOVERNMENT INTEREST

The invention described herein may be manufactured, used, and licensed by or for the United States Government for governmental purposes without the payment of any royalty.

BACKGROUND

1. Technical Field

Oculometers are used to measure the eye gaze direction, as well as the fixation duration and dual eye binocular convergence point. Such oculometers have many potential applications in the medical, scientific, engineering, manufacturing, military, and entertainment domains. Example applications include use of an oculometer as a tool for the medical diagnosis of ocular functions, as an aid to the paraplegic handicapped, for the measurement of ocular functions and workload in human factors studies, as a measure of subject training, as a tool for fatigue monitoring, as part of an electronic safety net to detect performance degradation due to pilot incapacitation in piloted and tele-operated vehicles, as a component of an electronic intelligent pilot-vehicle interface used for adaptive aiding in piloted and tele-operated vehicles, for task scan analysis including measuring situation awareness, for human operator control of machines and interaction with computer games, and for advertisement and usability analysis. Oculometers can be designed for use with head-mounted video displays such as those that have been developed for virtual reality, stereographic displays, monocular or binocular vision helmet-mounted displays, and night vision goggles. These displays are used in piloted helicopters, vehicles, and control stations for teleoperated robotics.

2. Description of the Related Art

Prior art oculometers typically comprise a light source that illuminates the eye to be tracked, and a single light sensor that captures rays of light that are reflected from the eye. Although such oculometers provide an indication of eye position and, therefore, gaze direction, the use of a single light sensor presents various potential limitations or drawbacks. For example, a single sensor may not receive the rays reflected off of the cornea or eye interior in cases in which the user's gaze is fixed upon an object positioned at an extreme angle relative to the forward-looking direction (e.g., when the wearer is gazing laterally). As another example, if the single sensor is used to collect image data that is used to locate features in the eye of interest in three-dimensional space, multiple images may need to be captured over time, thereby increasing processing time and potentially introducing error due to eye movement over the duration in which the image data is captured.

SUMMARY

Disclosed are systems and methods for tracking the eye. In one embodiment, a method for tracking the eye includes acquiring stereo images of the eye using multiple sensors, isolating internal features of the eye in the stereo images acquired from the multiple sensors, and determining an eye gaze direction relative to the isolated internal features.

BRIEF DESCRIPTION OF THE DRAWINGS

The disclosed systems and methods can be better understood with reference to the following drawings. The components in the drawings are not necessarily to scale.

DETAILED DESCRIPTION

Disclosed herein are systems and methods for tracking an eye. More particularly, disclosed are eye-tracking systems and methods that employ multiple light sensors that provide image data that is processed to determine at least a gaze direction of an eye.

Figure 1:
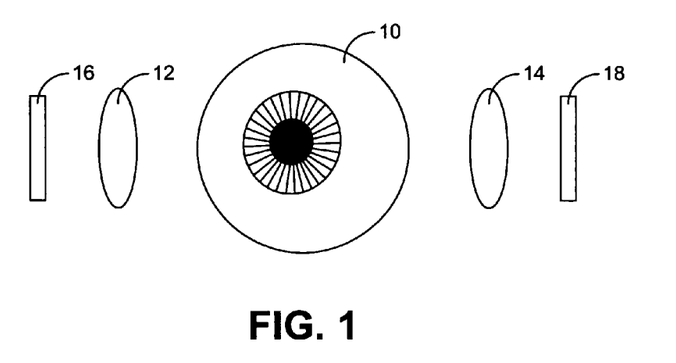
FIG. 1 is a schematic diagram of an eye being tracked by components of an eye-tracking system.

Referring now to the drawings, in which like numerals indicate corresponding parts throughout the several views, FIG. 1 illustrates an eye 10 of a user (e.g., a wearer of an eye-tracking mechanism). Positioned on opposite sides (e.g., opposed lateral sides) of the eye 10 are optical systems 12, 14 and light sensors 16, 18. The optical systems 12, 14 each comprise one or more lenses and/or mirrors that are used to direct and focus light that reflects off of the eye 10 on their associated light sensors 16, 18. The light sensors 16, 18 receive the reflected light (i.e., light rays), which is used to determine the gaze direction of the eye. More particularly, the light sensors 16, 18 generate two-dimensional "stereo" images of the eye 10 that can be used to calculate the optical axis and visual axis of the eye. Although the optical systems 12, 14 and the light sensors 16, 18 are shown and have been described as being positioned on opposite sides of the eye 10, other configurations are possible. One such configuration preferred for use with this invention, consists of sensors with light collecting optics that are positioned on opposite sides of the central axis of sight for the optical device. As shall be elaborated, the optical device consists of a light source, optical systems to collect the light reflected from the eye, and sensors matched to the optical systems to convert the light images to electrical outputs. In the preferred embodiment, the light collecting optics for the sensors are positioned so as to collect stereo images (i.e., slightly displaced two-dimensional images) of the eye as much as possible. Moreover, although two light sensors 16, 18 are shown and have been described, a greater number of light sensors could be used, if desired, for example sensors with optics positioned about the sides of the eye to cover the full range of viewing directions.

Figure 2:
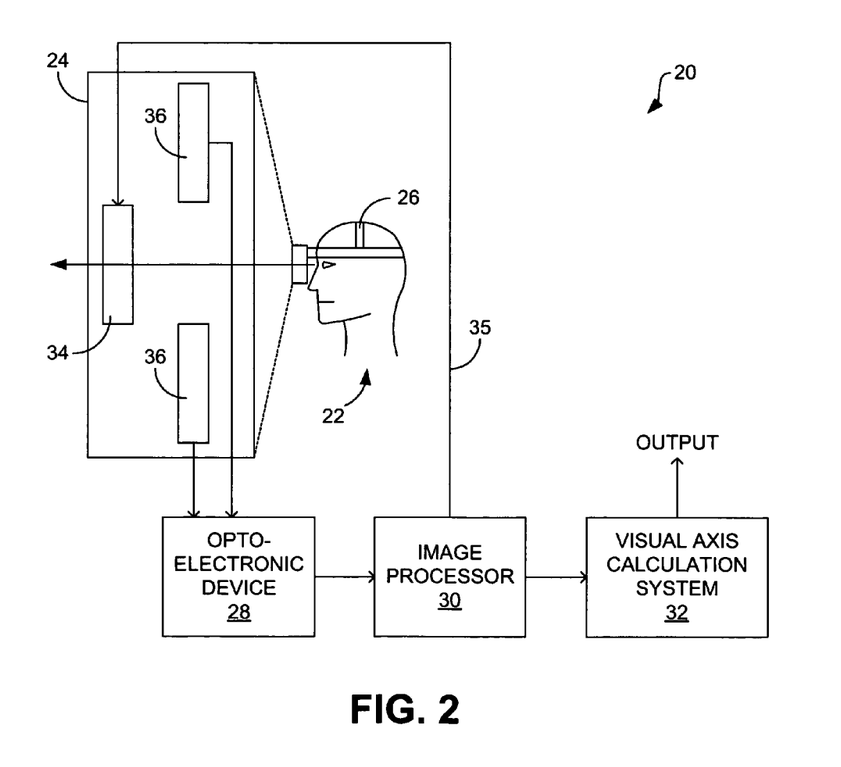
FIG. 2 is a block diagram of a first embodiment of an eye-tracking system

Referring to FIG. 2, illustrated is a first embodiment of an eye-tracking system 20 that can be used to determine the gaze direction of an eye of a user 22. The tracking system 20 comprises several components that are similar in configuration and/or function to components disclosed in U.S. Pat. No. 6,120,461, which is hereby incorporated by reference in its entirety into the present disclosure.

As is shown in FIG. 2, the tracking system 20 includes an optical device 24 that is mounted on a headset 26 that is donned by the user 22. In addition, the tracking system 20 includes an opto-electronic device 28, an image processor 30, and a visual axis calculation system 32. The optical device 24 comprises a light source 34 and two light sensors 36, with associated optical systems and opposed light collecting optics. The light source 34 is configured to, under the control of the image processor 30, shine light on an eye of the user 22. By way of example, the light source 34 comprises a display or one or more light-emitting diodes (LEDs). In cases in which the light source 34 comprises multiple light elements (e.g., pixels of a display or individual LEDs in an LED array), the elements of the light source can be sequentially illuminated by a control signal generated by the image processor 30 and delivered to the light source via control line 35. The light sensors 36 detect the light reflected from the user's eye, via the optical systems from the corresponding light collecting optics, and output analog image signals to the opto-electronic device 28.

The opto-electronic device 28 receives the image signals generated by the sensors 36, isolates specular reflections created by the light source 34, determines image coordinates of the reflection points on the corneal surface, and outputs signals to the image processor 30. The image processor 30 isolates various pertinent features (i.e., internal features) of the eye's anatomy from images captured by the sensors 36, for instance captured simultaneously in an instant in time or captured sequentially over a finite period of time. In cases in which images are captured simultaneously, different colored light elements can optionally be used to illuminate the eye so that the origin of reflected light can be determined (i.e., from the light's wavelength). By way of example, features of the eye that are isolated by the image processor 30 include the apparent pupil and the inner structures of the eye including the sphincteral pattern of the iris and the retinal capillary network. Once the eye features are identified, their locations (i.e., coordinates) within the two-dimensional images are determined by the image processor 30 and those locations are output as digital signals to the visual axis calculation system 32.

Operation from this point depends upon the particular configuration of the visual axis calculation system 32. Generally speaking, however, the visual axis calculation system 32 receives the data output by the image processor 30 and uses that data to calculate the optical axis of the eye, from which the visual axis and the gaze direction can be determined. More particularly, the visual axis calculation system 32 runs several processes or routines that compute the visual line of sight. This information can then be output from the visual axis calculation system 32 and used, for example by a digital computer, to determine various information such as: the workspace line of sight, eye fixations, gaze points, and the binocular convergence point for a dual-eye system. As is described in the following, the visual axis calculation system 32 may comprise one or more of a digital processor, a stereo reconstructor, and opthalmometric ray tracer that are used to determine the visual axis and gaze direction.

Figure 3:
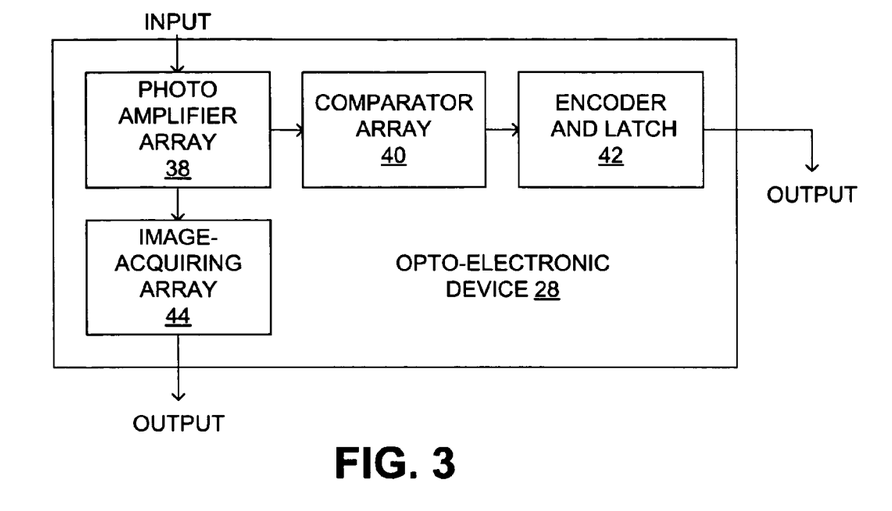
FIG. 3 is a block diagram of an embodiment of an opto-electrical device shown in FIG. 2.

Referring now to FIG. 3, illustrated is an example embodiment of the opto-electronic device 28 shown in FIG. 2. The illustrated embodiment has particular advantages for processing images from multiple sources, or a source with multiple elements, under sequential control of the processor 30. As is indicated in FIG. 3, the opto-electronic device 28 can comprise a photo-amplifier array 38, a comparator array 40, an encoder and latch 42, and an image-acquiring array 44. The photo-amplifier array 38 amplifies the analog signals received from the sensors 36 and outputs amplified signals to the comparator array 40 and the image-acquiring array 44. The comparator array 40 isolates the amplifier element(s) that first respond(s) to the illuminating element of the light source 34 and provides an electrical input to the encoder and latch 42. The encoder and latch 42 is controlled, for example, by the image processor 30 (FIG. 2), to output an electrical signal for each light source to the visual axis calculation system 32 via the image processor 30. The electrical signal contains the address of the first-responding amplifier and thereby maps the location of the specular reflection of the light source in the photo-amplifier array 38. In turn, the encoder and latch output causes the output of the amplifier element to be suppressed in the photo amplifier array 38 during the image acquisition period, resulting in an image of the diffused reflections from the inner surfaces of the eye. The image-acquiring array 44, outputs signals to the image processor 30, for instance to a charge-coupled device (CCD) array or a random-access memory (RAM) cache of the image.

While the above hardware has been described as an example, the functions that hardware provides can, alternatively, be performed in a pre-image processing stage in which the image data collected in the photo amplifier array for a given light source is thresholded in the comparator array to locate the specular reflection. The array address of the reflection point can then be output to the image processor while the reflection image is masked from the array before being added to the image-acquiring array. The image-acquiring array is outputted to the image processor for each sensor at the end of the source activation cycle and reset by the image processor before the cycle is repeated.

Figure 4:
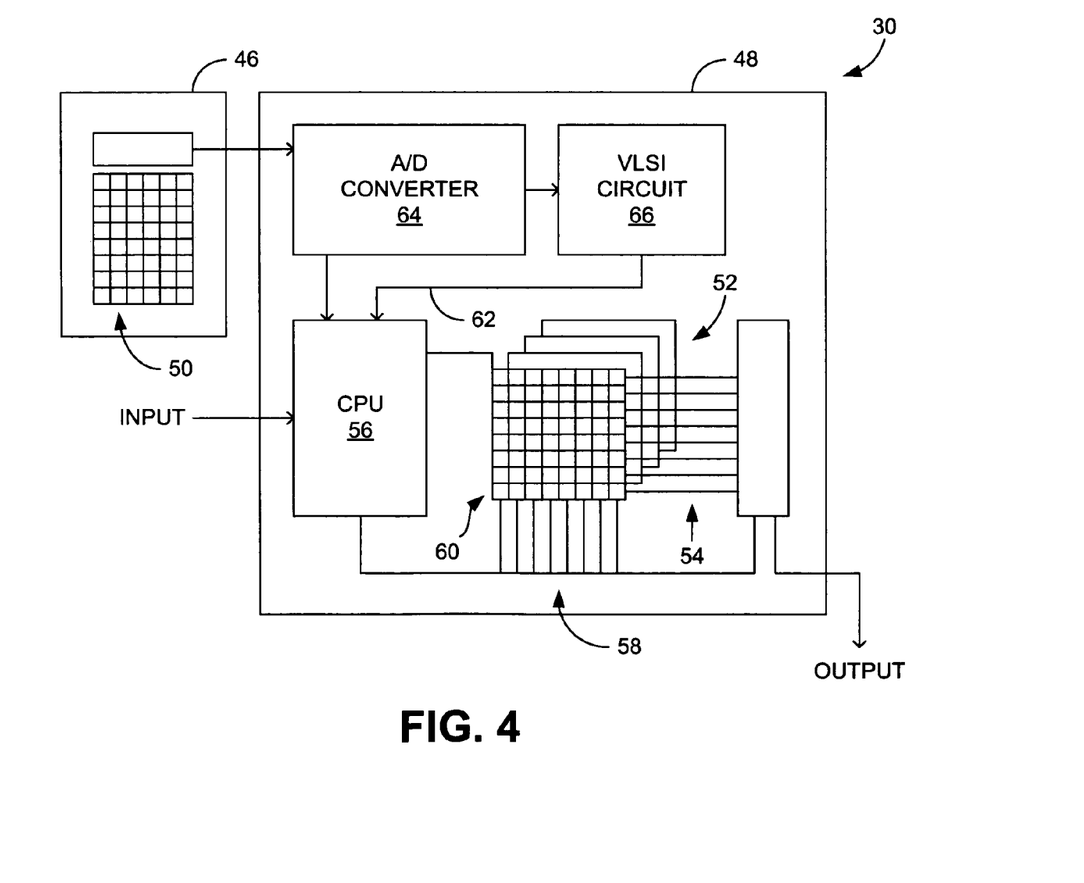
FIG. 4 is a block diagram of an embodiment of an image processor shown in FIG. 2.

FIG. 4 illustrates an example architecture for the image processor 30 and the interfacing of an image accumulator 46 and an image processing device 48 that can be used to isolate image features of the eye's anatomy. In the illustrated embodiment, the image accumulator 46 is a CCD that, for example, comprises photosensitive metal-oxide-silicon (MOS) capacitor elements arranged in a CCD array 50. With reference back to FIG. 3, array elements of the photo-amplifier array 38 receive analog light inputs from the sensors 36. Feature isolation is performed on the image accumulated by the image accumulator 46 as mapped from the image-acquiring array 44 by the image processing device 48.

In the illustrated embodiment, the image processing device 48 is embodied as a stack 52 of two dimensional very-large-scale-integrated (VLSI) circuit arrays made of conductive metal-oxide-silicon (CMOS) wafers. Each array in the stack 52 comprises identical digital processing elements that are matched between arrays by data bus lines 54 for image processing. The arrays are controlled by a central processing unit (CPU) 56 with common address and control bus lines 58. The CPU 56 operates with a clock, instruction decoder, register, arithmetic and logic unit, and access to a memory cache with a stored program for stack control. The initial array of the stack 52 is the digital memory cache 60 that stores the digitized images. The remaining arrays of the stack 52 comprise digital memory, comparators, counters, accumulators, and replicating elements. In operation, the CPU 56 writes numerical values to the array elements in the stack 52, operating the arrays en masse through the data and control bus lines 54, 58.

The array elements of the stack 52 perform conventional digital functions: (1) the memory elements perform store, shift, invert, Boolean logic OR function, and readout; (2) the accumulators store, add, and readout; (3) the replicating elements input, output, and perform stack control; (4) the counters count in and shift out; and (5) the comparators store reference values and output whether the input is greater, equal, or lower in value. The inputs to the stack 52 are the digital memory cache 60 and the pupil image moments 62. The output of the stack 52 is a memory-mapped list of the image features (e.g., spectral reflection point and structural eye features) and their image positions.

The accumulated image is transferred to the digital memory cache 60 from the CCD array 50. This may be accomplished by means of clocked serial bucket brigade downloaded to an analog-to-digital converter 64 with an analog input and a digital output. In that process, the output is read as a serial digital input by the very-large-scale-integrated (VLSI) circuit 66. The circuit 66 can, for example, comprise a video moment generator chip that is used to compute the image moments of the pupil and is made up of CMOS elements. In such a case, the chip comprises a digital comparator for thresholding, and counters, shifters, adders, registers, and a programmable logic array (PLA). The digital comparator separates the serial digital input for the pupil image intensity from that for the iris and the sclera. The digital elements perform recursive moment computations on the resulting binary image under the control of the PLA. At the end of the serial transfer, the circuit 66 outputs the elliptical moments of the pupil image such as the centroid, the principal and minor axes, and deviations from these axes.

In preparation for feature processing, the pupil image is isolated by the stack 52. The CPU 56 reads the pupil image moments from the VLSI circuit 66 following transfer of the digitized image to the digital memory cache 60. The CPU 56 isolates the portion of the image containing the pupil by computing a template from the elliptical moments and masking the image array cache. This is done by, for example, writing "ones" into the elements of a memory array which match the pupil's template and "zeros" into the remaining elements. The CPU 56 then uses an accumulator array to multiply the elements of the template array with the matched elements of the image array, and writes the products en masse to produce a masked-memory array.

Figure 5:
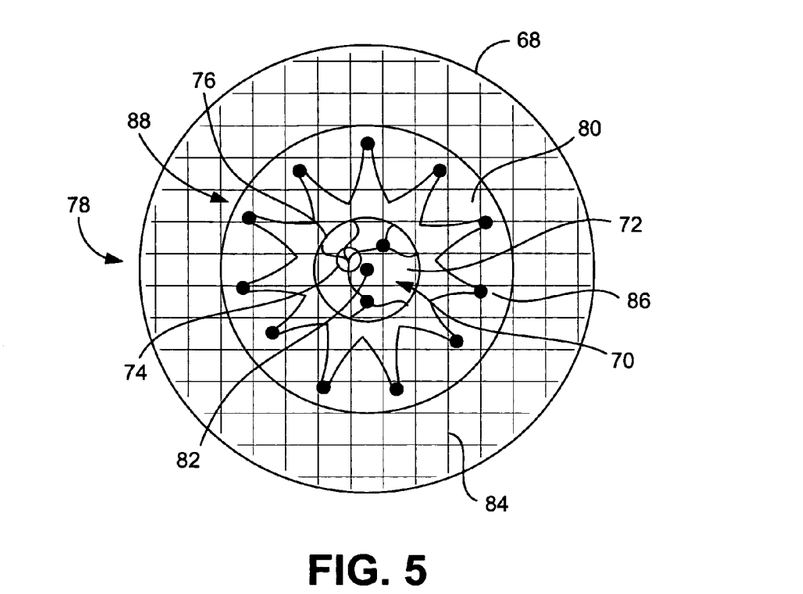
FIG. 5 is schematic view of an image of an eye with corneal reflection points and internal structural features identified in the image.

FIG. 5 illustrates an example procedure for isolating features of the eye using the image processor shown in FIG. 4. The following procedure is performed on both "stereo" images obtained from the sensors 36. In particular, the procedure is performed on separate two-dimensional images that are captured by the sensors 36 (from different positions relative to the eye) simultaneously or in close sequence such that the image processor 30 isolates the pertinent eye features from two different perspectives. The procedure is applied separately to each of the independent sensor images.

Following isolation of the pupil image, the apparent pupil can be parameterized as a centroid and elliptical axes. Such parameterization can be used for reference by a stereo reconstructor (see FIG. 9) in matching features across stereo images. The apparent pupil is used to segment the image into two separate regions: the apparent iris and the retinal fundus. From those two regions, the stack 52 can abstract key image features of the subject eye 68 including the sphincteral cusps of the iris and the capillary network of the retinal fundus. With reference to FIG. 5, vascular capillary network 70 radiates from the optic disk 74 at the back of the retina where the optic nerve (second cranial nerve) enters the eyeball. The portion of the retinal fundus 72 that is visible in the image is determined by the diameter and orientation of the pupil 76. For reference, the figure shows the sclera 78, the cornea 80, and the pupil centroid 82 as they appear in an image of the eye. Also shown is an overlaid grid 84 of corneal reflection points that are not part of the image, but that correspond to the table of reflection points for the sources that are generated by the image processor 30 from the latch outputs. The analysis of the vascular network is performed through a series of consecutive image processing steps in which: (1) the pupil image is enhanced with histogram equalization, (2) the vascular network is enhanced with spatial gradient templates for edges and lines, (3) the network is segmented by binary thresholding, and (4) the junction points of the network segments are isolated as key features.

The stack 52 can further isolate the cusps 86 of the pigmentary pattern on the sphincteral muscles of the iris 88, the opaque contractile diaphragm performed by the pupil. The sphincteral muscles contract or dilate the iris 88 with changes in ambient light and accommodation. While the pattern changes with contraction, the general shape defined by the cusps 86 remains invariant and unique to the individual. The stack 52 isolates these key features through a series of consecutive processing steps, the first of which comprising isolation of the iris image from that of the eye image. The remaining steps are similar to the vascular network analysis: (1) the iris image is enhanced with histogram equalization, (2) the outline of the pigmented portion of the iris is enhanced with spatial gradient templates for edges and lines, (3) the outline is segmented by binary thresholding, and (4) the cusp points of the outline are isolated.

The stack 52 isolates the iris image by intensity thresholding and binary equalization of the digitized eye image with removal of the pupil image. The intensity thresholding and binary equalization are performed by computing a threshold reference value with the histogram technique, and then using a replicator array to write the reference value to a comparator array. The gray scale intensities of the digital memory cache 60 are then compared en masse, under control of the CPU 56. In this process, "zeros" are written to a memory array for intensities that are equal to or less than the threshold, and "ones" for those that are greater than the threshold.

The stack 52 computes the image moments from the thresholded memory array. The CPU 56 writes the moment coefficients to the elements of an accumulator array as a function of the coordinates of the element in the array and the moment orders. The accumulator array repeatedly adds en masse the thresholded gray scale intensities according to the corresponding moment coefficients, and the accumulated sums are written to the memory array. The sums are accumulated as the contents of the memory array are shifted along the columns (or rows). This continues as the contents are shifted along the row (or column), following writing the summed column (or row) results to the memory array. The CPU 56 reads the array total as the value of the image moment. This action is repeated for all combinations of image moments of second order or less: (0,0), (1,0), (0,1), (2,0), (1,1), and (0,2). The elliptical central moments, comprising the centroid, principal and minor axes, and deviations from the axes of an elliptic representation, are then computed from these values. Finally, the image of interest is isolated by masking the image memory array with the thresholded memory array.

In some embodiments, the stack 52 computes an intensity histogram for an isolated image by first loading a comparator array with reference intensity levels, and then shifting the masked image array past the comparator, while counting the occurrences of the levels. More specifically, the CPU 56 writes reference values into the columns (or rows) of a comparator array with a replicator array, where the reference values are the same for each column (or row) and the values are indexed from zero to the highest intensity level. The contents of the masked memory plane are then shifted along the rows (or columns) of the array in a toroidal manner, while a counter array counts the comparator's "equal conditions." The counted values in the counter array are transferred to a memory array, and then summed in an accumulator as the memory array values are shifted along the columns (or rows). Finally, the CPU 56 reads the histogram distribution from the bottom row (or column) of the accumulator.

The stack 52 can enhance the intensity contrast of the isolated image with histogram equalization. The CPU 56 computes a histogram equalization mapping from the intensity histogram. Reference values are written into the columns (or rows) of a comparator array with a replicator array, where the reference values are the same for each column (or row) and the values are indexed from zero to the highest intensity level. The corresponding mapping function values for the histogram equalization are written to the elements of an accumulating array. The mapping function values are then written en masse to an enhanced memory array for the comparator's "equal condition" as the contents of the masked memory array and the enhanced memory array are shifted in step along the rows (or columns) of the array in a toroidal manner.

The stack 52 can further enhance the line structure in the isolated image with a spatial gradient template. In this process, the CPU 56 first zeros a destination accumulator array, and then performs a sequence of template matching processes on the enhanced image array. The template matching process first zeros a matching accumulator array, and then writes template weight values to an accumulator array. The enhanced image array is multiplied en masse by the template weights, and the products are added to the matching accumulator array. The enhanced image array is then shifted in turn left, right, down, up, and along each diagonal; and the above template weighting process is repeated for each shift. The absolute values of the contents for the template matching are then added to the destination accumulator array. This template matching operation is repeated for each template in the orthogonal set of line matching templates. Finally, the contents of the destination accumulator are written to a line-enhanced memory array.

The stack 52 segments the enhanced line structure (e.g., either a retinal capillary network or a pigmentary outline) by binary thresholding. An intensity histogram is first computed for the edge enhanced image, and a selected threshold value is then written as a reference value to the elements of a comparator array. The edge-enhanced image is compared en masse to the threshold value. A "zero" or "one" is written to a memory array depending upon whether the intensity of an element of the image is less than or equal to the threshold value, or if it is greater than the threshold value.

The stack 52 isolates the junction points of the line segments by counting with an accumulator array the number of neighboring pixels that are "one" for each "one"-pixel in the segmented image. For the junctions of the capillary network, the count is compared to a threshold of three with a comparator array; a "zero" is written to an isolation memory array for a count that is less than the threshold and "one" is written for a count that is equal to or greater than the threshold. For the sphincteral cusps on the iris, the count is compared to a threshold of two; a "one" is written to an isolation memory array for a count less than the threshold and "zero" is written for a count that is equal to or greater than the threshold.

The CPU 56 stores the image coordinates of the junction points of the network segments in cache memory. This is done by reading the isolation array with the CPU 56 as the elements are shifted by rows (or columns) and columns (or rows) until all elements are read, and storing the row and column addresses of those elements that are "ones." Finally, at completion of the image feature isolation, the CPU 56 outputs to a memory mapped area, the pupil moments, and the image coordinates of the retinal network segment junctions and the iris-sphincteral cusps, along with the image locations of the specular reflection points. This process is repeated for all sensor images collected during the source element activation cycle. It is noted that although the tasks described above in relation to FIG. 5 are described as being performed by specific hardware, these tasks could alternatively be performed by a CPU using an appropriate algorithm.

Figure 6:
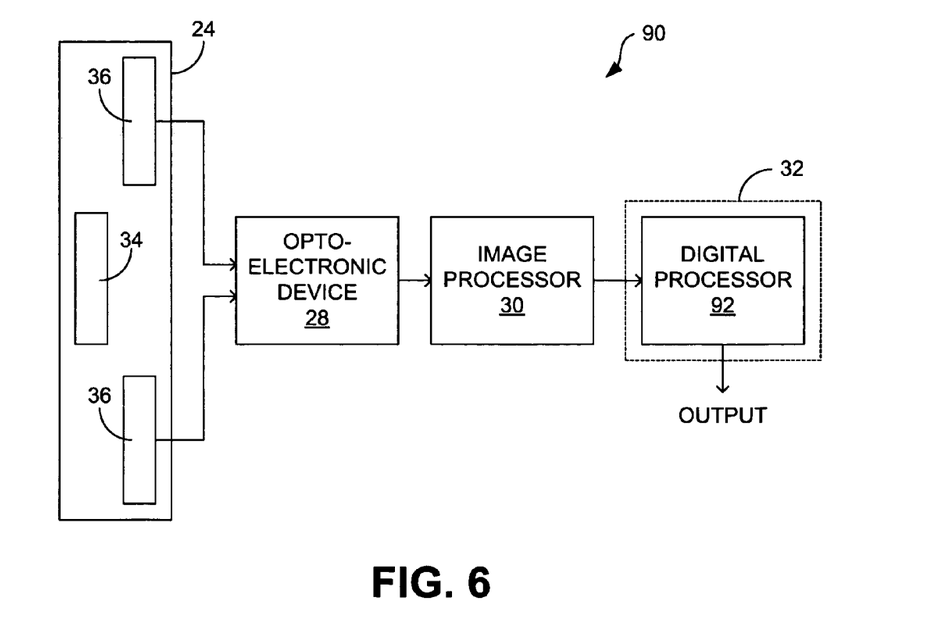
FIG. 6 is a block diagram of a second embodiment of an eye-tracking system.

FIG. 6 illustrates another embodiment of an eye-tracking system 90. The components of the system 90 are similar to those of the system 20 described with reference to FIGS. 2-5. As is indicated in FIG. 6, however, the visual axis calculation system 32 comprises a digital processor 92. The digital processor 92 receives the parameters output from the image processor described in the foregoing, i.e. the image coordinates of the centroid and elliptical axes of the apparent pupil and those of the sphincteral cusps and the capillary network, and estimates the visual axis from these parameters for each stereo image using an algorithm with calibration parameters derived from an initial calibration procedure. The use of features from the two stereo images enables accurate estimation of the visual axis over a wider range of eye movements than is possible with the coverage of a single sensor image. This is true since a lateral gaze that falls outside the image processing range of one sensor 36 will still be within the range of the other sensor 36. Although the system 90 provides a viable method to track the eye, the accuracy of the estimate is limited by the accuracy with which the algorithm can determine the gaze direction using the apparent locations of the eye features in the two-dimensional stereo images, as opposed to the actual locations of the features within the interior of the eye.

Figure 7:
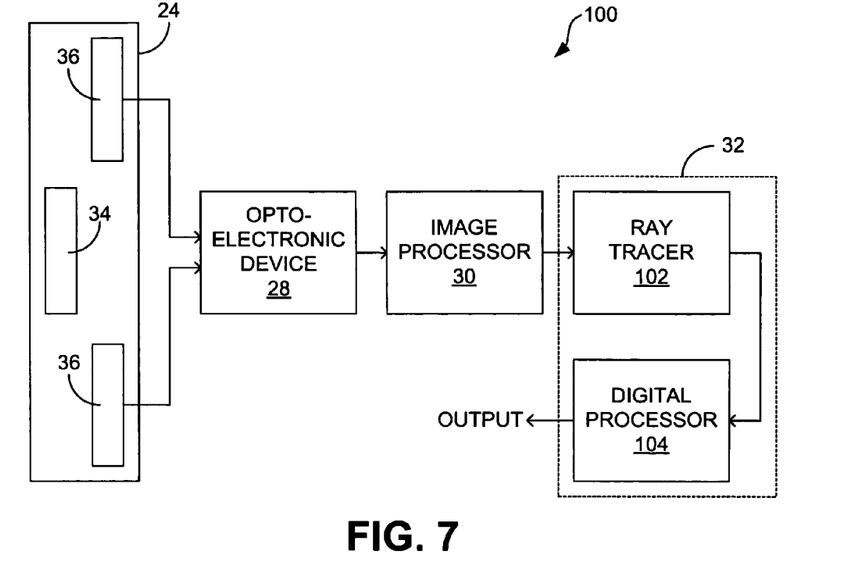
FIG. 7 is a block diagram of a third embodiment of an eye-tracking system.

FIG. 7 illustrates a further embodiment of an eye-tracking system 100. In this embodiment, the visual axis calculation system 32 includes a digital processor 104 and an opthalmometric ray tracer 102. The ray tracer 102 comprises a processor and/or software that calculates the three-dimensional coordinates of the pertinent features of the eye, and therefore the optical axis and visual axis, using ray-tracing techniques. In the system 100, the opto-electronic device 28 isolates the specular reflection points and the image processor 30 isolates the internal features of the eye in the manner described above for each stereo image. The ray tracer 102 then computes the center and radius of the anterior spherical corneal surface from the specular reflection points, and the locations of various internal features of the eye including, for example, the pupil centroid, the iris cusp points, and the capillary system in the inner structure of the eye. This is done from the image locations of these features and the geometry of the cornea and the locations of the source and sensors in the optical device. The ray tracer 102 then outputs the origin and orientation of the optical axes to the digital processor 104, which in turn outputs the origin and directional cosines of the visual axis.

Figure 8:
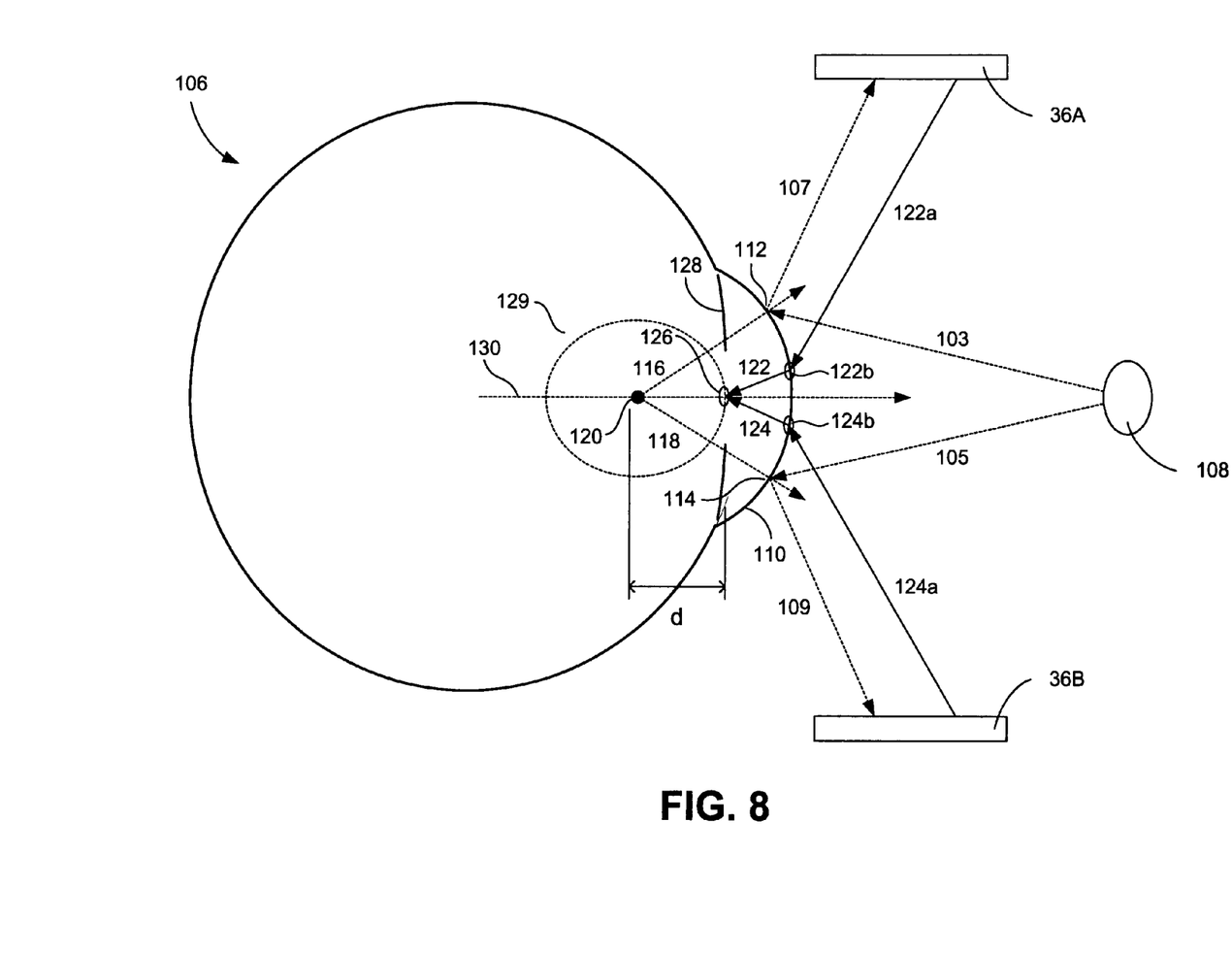
FIG. 8 is a schematic view of a cross-section of an eye depicting an embodiment of opthalmometric ray tracing to determine a pupil center.

FIG. 8 illustrates an example ray-tracing technique performed by the ray tracer 102. In particular, FIG. 8 shows a cross-sectional view of an eye 106 with the geometry of the ray-tracing technique. Here, emitted rays 103, 105 from a light source element 108 are reflected from the corneal surface 110 (as reflected rays 107, 109) to the sensors 36A and 36B from surface reflection points 112 and 114, respectively. The emitted (103, 105) and reflected (107, 109) rays are coplanar with the surface normals 116 and 118 drawn from the corneal center 120. The locations of the reflection points 112, 114 on the corneal surface 110 are computed from the source and sensor pairing relations for the emitted (103, 105) and reflected (107, 109) rays. In this manner, the ray tracer 102 computes a geometrical representation of the corneal anterior surface, here represented in the figure by a spherical section with a center and radius, from the set of reflection points (i.e., specular reflections) indexed by the light source and sensor pairing over a source activation cycle.

Important to the successful application of this technique is the proper parametric representation of the corneal surface 110. The corneal surface 110 may be calculated as a spherical section with center 120 in the coordinate system of the optical device 24 (FIG. 2) holding the sources 34 and sensors 36 with the memory-mapped image locations of the surface reflection points, such as 112 and 114. In an alternative embodiment, an ellipsoidal fit is determined for the corneal surface 110 with orientation axes because the corneal surface is more basilar with a slightly ellipsoidal shape than spherical. In a further alternative embodiment using geometric modeling, a grid of triangular meshes of basilar segments is used to define the corneal surface.

The ray tracer 102 then uses the computed model of the corneal surface 110 to trace the images of the eye features isolated by the image processor 30 (FIG. 7) back to the inner structure sources. With further reference to FIG. 8, the ray tracer 102 computes the traces 122a, 124a of the refracted rays for the pupil center 126 back from the sensors 36a, 36b to the locations of the apparent pupil images 122b, 124b on the corneal surface 110. From the locations of these apparent images 122b, 124b, the ray tracer 102 then computes the traces 122, 124 of the transmitted rays back to the pupil center 126, which lies in a plane defined by the iris 128 and along the optical axis 130 at a distance d from the corneal center 120. These back-traced rays (identified by traces 122, 124) are the reverse of the light rays refracted by the surface of the corneal surface 110. The true rays originate from the inner structure of the eye and are transmitted to the surface points (e.g., points 122b, 124b) where they are refracted toward the sensors 36a, 36b.

The distance d is determined during the initial calibration for the pupil, and conceptually defines a feature sphere 129. The feature sphere 129 is a mathematical construction that is centered at the center of the cornea (idealized itself as a sphere), and has the location of the inner structure feature on its surface. Thus, a ray traced back for a single sensor will intersect the surface of the feature sphere 129 at the location of the feature itself. The location of the ray intersection is calculated from the computed radius of the corneal model and that of the feature sphere, the radius of which is determined through the calibration process. The pupil center 126 lies on the sphere 129 at the point at which the back-traced transmitted rays 122, 124 intersect the sphere. Since the pupil is positioned in front of the corneal center 120, a correct solution for the ray tracing occurs with a negative value for the vector dot product formed from the directional cosines of the back-traced transmitted rays 122, 124 and the outer-directed surface normal from the corneal center 120 to the sphere 129 at the ray intersection point.

This technique of opthalmometric ray tracing may further be applied to determine the positions of the capillary junctions of the retinal fundus and the cusps of the sphincteral pattern on the iris. In such a case, the ray tracer 102 computes the locations of these structural features using the memory-mapped eye image locations from the image processor 30. The light rays from the features are transmitted through the eye and refracted by the cornea to reach the image plane of the sensor for processing by the accumulator 46 of the image processor 30. The locations of the refraction points are computed from the image coordinates of the feature, the locations and orientations of the corresponding sensors, and the geometry of the corneal surface. The directional cosines for the transmitted rays are computed from the corneal index of refraction and Snell's law relating the angle of incidence to the angle of refraction. In turn, the location of each feature is computed from the intersection of the back-traced transmitted ray with the corresponding feature sphere. The location of the feature is the point at which the back-traced refraction rays intersect the sphere.

Since the iris 128 is positioned in front of the corneal center 120, a correct solution for the ray tracing of the cusp features occurs with a negative value for the vector dot product formed from the directional cosines of the back-traced ray and the outer-directed surface normal from the corneal center to the cusp feature sphere at the ray intersection point.

Unlike the iris 128, the retinal fundus lies behind the corneal center. Therefore, a correct solution for the locations of the capillary junctions occurs for a positive vector dot product. The computations for the features of the retinal network include transmission through the crystalline lens and the internal vitreous body. The indexes of refraction for the aqueous humor and vitreous body are the same at 1.33; the index for the crystalline lens at 1.42 is nearly the same as that for the cornea at 1.38. The fundus capillaries are on the retina behind the crystalline lens within the eye, and the corresponding images acquired by the sensors depend upon the visual accommodation distance. However, the distribution of the fundus capillary junctions about the visual axis remains invariant of lens accommodation and this relation is used in the computations.

The ray tracer 102 computes the optical origin and the optical and median axes by best fit to a three-dimensional model of the computed values. These are for the corneal optical center and axes, the pupil optical center, and the optical locations of the key features for the capillary network of the retinal fundus and the sphincteral pattern of the iris. The pupil optical center and the optical locations of the capillary network and the sphincteral pattern can be computed using the opthalmometric ray tracing method as above. Separate sets of these values are computed for each of the stereo images, and the ray tracer 102 uses a best-fit approach to match feature locations across images. In turn, the averages of the locations of the matched features are used to best fit a three-dimensional model for computations of the optical origin and the optical and median axes. The ray tracer 102 computes the center and directional cosines for the optical and median axes of the eye in the coordinate system of the optical device 24. The roll of the eye is computed in an orthogonal set of median axes that are perpendicular to the optical axis to complete the specification of the optical orientation.

The ray tracer 102 produces an accurate description of the optical axes and center in the display coordinate system. This is the output of the ray tracer 102 to the digital processor 104 for computation of the visual axis. However, the visual axis extends from the first Gaussian nodal point of the eye (normally near the center of curvature of the corneal anterior surface) and is commonly perpendicular to the cornea; it is generally directed 5 degrees inwards to the optical axis and 2 to 3 degrees upward. The visual axis is defined by an origin point in the optical axes coordinate system and three directional cosines determined in an initial calibration process. These parameters defining the visual axis are transformed into coordinates for the optical device 24 from the relations for the optical axes. The result is an accurate specification of the visual axis.

Figure 9:
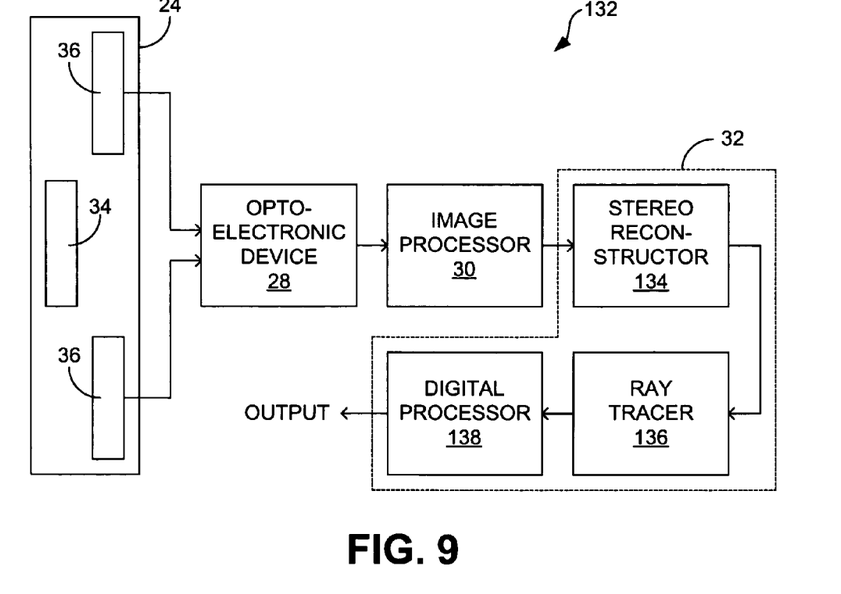
FIG. 9 is a block diagram of a fourth embodiment of an eye-tracking system.

FIG. 9 illustrates yet a further embodiment of a tracking system 132. In the system 132, the visual axis calculation system 32 includes a stereo reconstructor 134, a ray tracer 136, and a digital processor 138. The stereo reconstructor 134 matches the internal features isolated by the image processor 30 (e.g., the apparent pupil centroid, iris cusps, and capillary junction points) for the stereo images. In this process, the stereo reconstructor 134 uses the apparent pupil centroid and ellipsoidal axes in each image to locate the features in that image relative to the pupil. This process includes the computation of an apparent pupil optical axis from the corresponding elliptical major and minor axes, and locating the apparent features in the resulting coordinate system for each image. The reconstructor 134 then does a closest fit approach across multiple images of the feature locations to match and identify features. The output from the reconstructor 134 to the ray tracer 136 is an inner feature identifier for the features in each image. Included with the input to the ray tracer 136 are the image locations of the specular reflections (referenced by light source and sensor pairings), and the apparent pupil center, iris cusp, and retinal capillary junctions points (referenced by inner feature identifiers) for each stereo image. The ray tracer 136 computes the center and radius of the anterior spherical corneal surface from the image specular reflection points, and then computes the back-traced refracted rays for the pupil centroid, iris cusp, and retinal capillary junction points on the inner structure of the eye from the image coordinates from each image.

Referring back to FIG. 8, the ray tracer 136 computes the rays 122 and 124 for the pupil centroid 126 from the apparent images at 122b and 124b, respectively. However, these rays 122, 124 are identified by the stereo reconstructor 134 as corresponding to the pupil centroid 126, and the physical location of the feature is computed from the intersection of the rays 122 and 124. Equivalently, the ray tracer 136 can compute the back-traced rays for the inner features of the iris cusp and retinal capillary junctions as matched across images to determine the inner structure physical location of the feature from the intersection of the matched rays. Notably, in extreme viewing cases in which the user is looking so far to the side of the optical device that the pupil image is acquired by only one sensor, this ray-tracing technique (i.e., back-tracing across matched images) is not possible. In such cases, the ray-tracing technique described in relation to FIG. 7 can be used to compute the location of the feature from the intersection of the back-traced ray with the corneal-centered feature sphere determined from calibration.

The ray tracer 136 computes the origin and orientation of the optical axis and outputs this information to the digital processor 138, which in turn calculates and outputs the origin and directional cosines of the visual axis. The advantage of this process over that described in relation to FIG. 7 is that, by using the stereo reconstructor 134, feature location may be computed from the intersection of the multiple rays, and is therefore more accurate. Since the features have been identified in the stereo reconstruction process, the model fitting used to determine the optical axes has been replaced by a direct computational equation with the feature locations as predetermined variables. Furthermore, stereo reconstruction improves the determination of the feature spheres in situations in which only a single sensor image can be acquired, such as for lateral vision. Moreover, the calibration process is improved since a more accurate determination of the radii of the feature spheres can be made after the inner structure features have been located using the stereo reconstruction, rather than as part of the calibration process.

Irrespective of the particular configuration of the tracking system used to determine the optical and visual axes, data obtained from the tracking system can be further processed to make further determinations. For example, if a separate tracking system is used for each eye of the user, the binocular convergence point of visual gaze may be determined. To accomplish this, the visual axes are used as inputs and their closest point of intersection is computed to determine the convergence point.

Furthermore, as is described in U.S. Pat. No. 6,120,461, the output of the tracking system can be input into a separate digital computer or equivalent task-specific digital processor for control of display cues and other task relevant elements. In such a case, the digital computer can use the various visual parameters provided by the tracking system to compute the visual gaze point with regard to task workspace coordinates from an embedded knowledge of the workspace geometry and the head location and orientation in that space determined from a head position and orientation sensor. The computer can use those determined gaze points to determine control signals for the task-relevant elements including a display driver with output of display cue parameters. In such an implementation, an initial calibration process is performed under control of the digital computer to determine the relation between the optical parameters derived by the apparatus and the visual lines of sight. In one embodiment, these parameters comprise the image locations of the source specular points, and the apparent pupil centers and elliptical axes isolated for the images. In other embodiments, the parameters comprise the origins and directional cosines of the optical axes. In the calibration process, the digital computer receives as input the optical features (e.g., the origins and directional cosines of the optical axes of sight) in lieu of that for the visual lines of sight as the user looks at visual cues presented under computer control. The computer determines the relation between these features and the visual lines of sight and the relating values are stored in the digital processor of the eye-tracking system by the computer. This result may be in the form of an artificial neural network relating the optical features such as the source specular points and the apparent pupil centers and elliptical axes, or the origin and directional cosines of the optical line of sight, to the location and direction of the visual axis of the eye for each apparatus of the invention.

Figure 10:
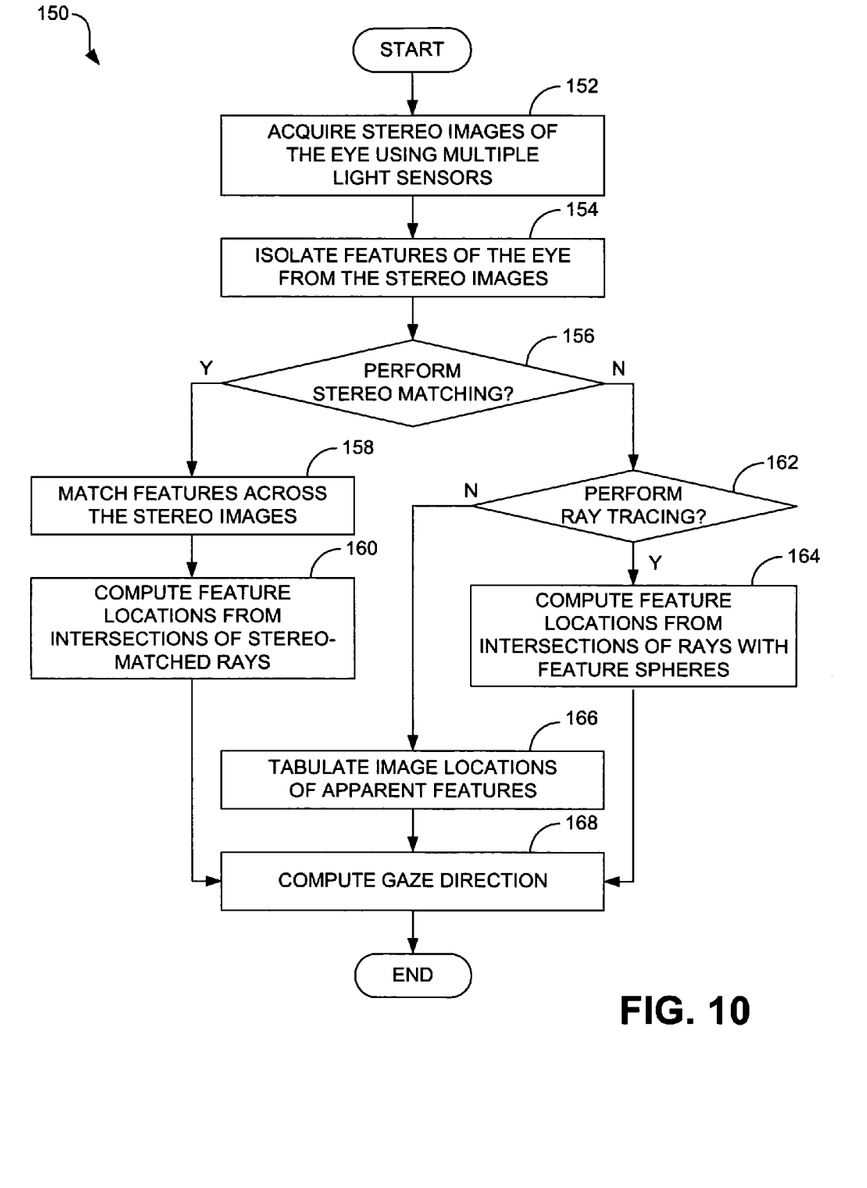
FIG. 10 is a flow diagram of a method for tracking an eye.

FIG. 10 is a flow diagram that describes a method 150 for tracking an eye in accordance with the processes discussed in the foregoing. Beginning with block 152, the system acquires stereo images of the eye using multiple light sensors. By way of example, two such sensors are used, each positioned at a different location relative to the eye such that the eye can be easily traced irrespective of the gaze direction.

In the image acquisition process, multiple light sources can be activated one at a time in a sequential cycle by setting a source count to zero and then incrementing the count to activate the source. During the activation of a source, the images acquired by the sensors are accumulated and, in some embodiments, processed one at a time by setting the sensor image count and then incrementing the count until all images have been accumulated. In such an image accumulation process, the sensor images are first threshold limited, and then masked to remove the source specular points, the image coordinates of which can be stored for reference. The cycle is continued until all sources have been activated. At that time, the accumulated images can be output for the source activation cycle.

Referring next to block 154, the system then isolates internal features of the eye from the accumulated images. In this process, the images can be accessed one at a time by first setting an image count to zero and then incrementing the count in similar manner to that described above. By way of example, the apparent pupil (and its centroid and elliptical axes) can first be isolated, followed by iris and retinal fundus images. Next, the image features comprising the apparent iris cusps and the retinal capillary junctions can then be isolated and, finally, the image coordinates of these image features can be abstracted and stored. This process is repeated for all accumulated images, and the image coordinates of the apparent features can be output in a set of files indexed by image.

With reference to decision block 156, flow from this point depends upon whether stereo matching is to be performed. This determination can depend upon the system design. Specifically, whether stereo matching is or is not performed can depend upon whether the system includes or does not include the stereo reconstructor 134 (FIG. 9). Alternatively or additionally, this determination can depend upon the image data that is acquired in block 152. Specifically, even in embodiments in which the system comprises the stereo reconstructor 134, stereo matching may not be possible if the user's gaze is so extreme that the pupil image is only acquired by one sensor. In such a case, no internal features of the eye can be "matched" across images from separate sensors.

If stereo matching is not performed, either due to the system design or lack of sufficient image data, flow continues down to decision block 162 described below. If stereo matching is performed, however, the isolated features across the stereo images are matched, as indicated in block 158. In this process, the image files can be accessed one at a time first by setting an image count to zero and then incrementing the count to access the corresponding file. The features in the file are then located relative to the pupil image centroid and elliptical axes for that file. This process is repeated until all image files are processed. The apparent features across the images can be matched by a closest fit of the relative locations. At this point, a file of apparent features annotated by matching identifiers can be output.

Referring next to block 160, ray tracing is performed to locate inner features of the eye by computing feature locations from intersections of stereo-matched rays (see discussion of FIG. 9). Important to this process is the input of the list of source specular points with image coordinates indexed by source and sensor and the files of image apparent features with image coordinates and matching identifiers described above. The system (i.e., ray tracer) first parameterizes the corneal anterior surface from the coordinates of the source specular points and the locations of the sources and sensors in the optical device 35. The system then locates the inner structure within the eye for the apparent features. In some embodiments, the features are processed one at a time first by setting a feature count to zero and then incrementing the count to access the images coordinates of the feature in all images. For each image, the refracted ray from the apparent feature is back traced to the inner structure of the eye.

With reference back to decision block 156, if stereo matching is not performed, again due to system design or lack of image data, flow continues to decision block 162 at which it is determined whether ray tracing is to be performed. This determination can depend upon the system design. Specifically, whether ray tracing is or is not performed can depend upon whether the system includes or does not include the ray tracer 102 or 136 (FIGS. 7 and 9). If no ray tracing is to be performed, flow continues to block 166 described below. If, on the other hand, ray tracing is to be performed, flow continues to block 164 at which the feature locations are computed from the intersections of the back-traced ray with the corresponding feature spheres separately for all images. The location of the feature is the average of the locations with the closest fit across images. This process is repeated for all features, and the inner structure coordinates of the features can then be output.

If no feature matching is performed (decision block 156) and no ray tracing is performed (decision block 162), flow continues to block 166 at which the image locations of the various apparent features isolated by the system (block 154) are tabulated.

Referring now to block 168, once ray tracing has been performed by matching rays (block 160) or feature spheres (block 164), or if no ray tracing was to be performed (block 166), the gaze direction is next computed. The manner in which this process is performed depends upon whether ray tracing was performed. If so, the inner feature coordinates are used to compute the origin and directional cosines of the optical axes and, in turn, compute the visual axis and gaze direction from relations derived in calibration and the gaze history. If, on the other hand, no such ray tracing is performed, the gaze direction is estimated using the isolated apparent image features.

The feature set used in the gaze computations can, in some embodiments, be automatically and dynamically selected depending upon the quantity of the features successfully isolated. For example, a lateral gaze by the user so far to the side that the pupil and inner structure falls outside of the acquisition range of the sensors can force the system to depend upon apparent image features. A more centered gaze will place more of the features within acquisition range of a sensor, and the ray tracing coupled with the feature spheres can provide the feature set. Finally, a forward gaze will place the full set of eye features within acquisition by the stereo sensors, and ray tracing coupled with matching rays can be used to provide the feature set. Of course, the range of flexibility will depend upon the optical design for the instrument.

As can be appreciated from the foregoing disclosure, the described systems and methods enable computation of gaze with increased accuracy. The increased accuracy is due to an improvement in the opthalmometric determination of the locations of the features of the inner structures of the eye, including the pupil center and the pigmentary cusp patterns on the sphincteral muscles of the iris. The improved determination is possible because, the structural features are located by the intersections of the multiple ray tracings from the opposing stereo images, a procedure which replaces the less accurate determination of a single back traced ray intersection with a corneal centered feature sphere derived in calibration for the single sensor design, the locations of the apparent images of the structure features used in the ray tracing are determined by the intercepts of the image projections with the corneal surface, a procedure replacing the less accurate derivation of the apparent image location by interpolating among multiple-source corneal reflections, and direct computational equation with the feature locations as predetermined variables replaces the model fitting used previously to determine the optical axes.

The aforementioned advantages are made possible by the use of a stereo reconstruction procedure using multiple light sensors with which the apparent images of the features are correlated across images. The accuracy of the calibration process is improved for the determination of the corneal centered feature spheres, which are used in gaze computations when only a single sensor image can be acquired such as for lateral vision. Because multiple light sensors are used in the procedure, relatively few, strategically placed light sources may be used instead of an extensive array of light sources as in prior systems and methods. Moreover, multiple sensor designs enable a wider coverage of the eye movement including extreme lateral angles, whereas present commercial designs are often limited in the extent of coverage to a central field of view. In contrast to existing designs, the disclosed system allows wider if not full coverage while taking advantage of the stereo image properties for increased accuracy.

Various computer logic has been described above. This logic can be stored on any computer-readable medium for use by or in connection with any computer-related system or method. In the context of this disclosure, a computer-readable medium is an electronic, magnetic, optical, or other physical device or means that contains or stores a computer program or routine for use by or in connection with a computer-related system or method. Logic can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

What is claimed is:

1. A method for tracking an eye in eye movement space, the method comprising:
   providing a means for illuminating the eye;
   providing a means comprising multiple sensors for acquiring stereo images of the eye from different spatial perspectives;
   acquiring stereo images of the eye using multiple sensors;
   isolating internal features of the eye from the stereo images acquired from the multiple sensors;
   isolating specular reflection points on a corneal surface of the eye, the specular reflection points resulting from reflections of light emitted from a plurality of light sources sequentially used to illuminate the eye;
   computing a center and radius of the spherical corneal surface using the specular reflection points;
   calculating three-dimensional coordinates of the isolated internal features within the eye by performing ray tracing;
   matching features across stereo images that are acquired by separate sensors, wherein the matching process makes use of the distribution of the features about apparent pupil elements common to both images
   wherein performing ray tracing comprises computing feature locations from intersections of stereo-matched rays, wherein the stereo-matched rays have been derived using a refractive computational process; and
   determining an eye gaze direction relative to the isolated internal features.

2. The method of claim 1, wherein acquiring stereo images comprises acquiring images from sensors which further comprise light collecting optics positioned on opposite sides of a central axis of sight within the eye movement space.

3. The method of claim 1, wherein isolating internal features of the eye comprises isolating one or more of a pupil centroid, sphincteral cusps of an iris, and a capillary pattern of a retinal fundus.

4. The method of claim 1, wherein determining an eye gaze direction comprises tabulating image locations of the isolated internal features from the stereo images and estimating a visual axis of the eye from the tabulated image locations using an algorithm and calibration parameters derived from an initial calibration process.

5. The method of claim 1, wherein calculating three-dimensional coordinates of the isolated internal features comprises calculating three-dimensional coordinates of a pupil centroid, sphincteral cusps of an iris, and a capillary pattern of a retinal fundus.

6. The method of claim 1, wherein performing ray tracing comprises computing feature locations from intersections of back-traced rays and feature spheres.

7. The method of claim 1, wherein the manner in which ray tracing is performed depends upon the stereo images that are acquired.

8. A system for tracking an eye movement space, the system comprising:
   means for illuminating the eye;
   means for acquiring stereo images of the eye from different spatial perspectives;
   means for isolating specular reflections on a corneal surface of the eye in the stereo images;
   means for isolating internal features of the eye in the stereo images; and
   means for determining an eye gaze direction relative to the isolated internal features, wherein the means for determining an eye gaze direction comprise a ray tracer that calculates a center and radius of the spherical corneal surface using the specular reflection points, and the coordinates of the isolated internal features of the eye relative to a computed corneal surface using ray-tracing techniques, and a stereo reconstructor that matches isolated internal features across stereo images acquired by separate sensors using a best fit feature vector approach; and
   wherein the ray tracer computes feature locations from intersections of stereo-matched rays, wherein the stereo-matched rays have been derived using a refractive computational process.

9. The system of claim 8, wherein the means for acquiring stereo images comprise separate sensors which further comprise light collecting optics positioned on opposite sides of a central axis of sight within the eye movement space.

10. The system of claim 8, wherein the means for isolating specular reflections comprise an opto-electronic device that receives image signals from the means for acquiring stereo images, said opto-electronic device further comprising means for electronically representing spatially optical corneal reflection,
    transmitted from said optical device.

11. The system of claim 8, wherein the means for isolating internal features of the eye comprise an image processor.

12. The system of claim 8, wherein the means for determining an eye gaze direction comprise a digital processor that estimates a visual axis from the isolated internal features using an algorithm with calibration parameters derived from an initial calibration procedure.

13. The system of claim 8, wherein the ray tracer computes feature locations from intersections of back-traced rays and feature spheres.

14. An eye gaze tracking system, comprising:
    a light source that is configured to illuminate a user's eye;
    light sensors that are configured to be positioned at different locations relative to the eye and capture stereo images of the eye from different spatial perspectives;
    an opto-electronic device that is configured to receive stereo images from the light sensors and isolate specular reflection points on a corneal surface of the eye that correspond to reflections of light emitted from the light source;
    an image processor that is configured to isolate internal features of the eye, compute a center and radius of the spherical corneal surface using the specular reflection points, and calculate three-dimensional coordinates of the isolated internal features within the eye by performing ray tracing;

a stereo reconstructor that is configured to match internal features isolated by the image processor across stereo images acquired by separate sensors, wherein the matching process makes use of the distribution of the features about apparent pupil elements common to both images; and a ray tracer that is configured to calculate the coordinates of the isolated internal features of the eye relative to a computed corneal surface from intersections of stereo-matched rays, wherein the stereo-matched rays have been derived using a refractive computational process.

15. The system of claim 14, wherein the light source comprises a plurality of discrete light-emitting elements, operationally connected to the said opto-electronic processor.

16. The system of claim 14, wherein the light sensors further comprise light collecting optics positioned on opposite sides of a central axis of sight within the eye movement space.

17. The system of claim 14, wherein the image processor is configured to isolate a pupil centroid, sphincteral cusps of an iris, and a capillary network of a retinal fundus of the eye.

18. The system of claim 14, wherein the ray tracer is configured to compute feature locations from intersections of back-traced rays and feature spheres.

19. The system of claim 14, wherein the ray tracer automatically computes the feature locations from intersections of stereo-matched rays if the stereo reconstructor is able to match isolated internal features across stereo images, and automatically computes feature locations from intersection of back-traced rays and feature spheres if the stereo reconstructor is not able to match isolated internal features across stereo images, such that the system dynamically alters the ray-tracing process upon the image data that is available.

* * * * *